United States Patent [19]

Ikeda et al.

[11] Patent Number: 4,623,789
[45] Date of Patent: Nov. 18, 1986

[54] FIBEROPTIC PROBE FOR BRAIN SCANNING WITH DETACHABLE CANNULA GUIDE

[75] Inventors: Masato Ikeda, Nara; Kenji Kurokawa, Hyogo, both of Japan

[73] Assignee: Shionogi & Co., Ltd., Osaka, Japan

[21] Appl. No.: 587,065

[22] Filed: Mar. 7, 1984

[30] Foreign Application Priority Data

Mar. 10, 1983 [JP] Japan .............................. 58-35110[U]

[51] Int. Cl.[4] ........................... H01J 5/16; A61M 5/00
[52] U.S. Cl. .................................... 250/227; 604/175; 128/634
[58] Field of Search ..................... 128/348.1, DIG. 26, 128/748, 634; 604/174, 175, 178; 250/227

[56] References Cited

U.S. PATENT DOCUMENTS

| | | | |
|---|---|---|---|
| 1,083,103 | 12/1913 | Jentzsch | 128/343 |
| 3,068,739 | 12/1962 | Hicks, Jr. et al. | 128/634 |
| 3,444,861 | 5/1969 | Schulte | 604/175 |
| 4,210,029 | 7/1980 | Porter | 128/634 |
| 4,235,232 | 11/1980 | Spaven et al. | 604/178 |

OTHER PUBLICATIONS

M. Ikeda and A. Matsushita, "Reflectance of Rat Brain Structures Mapped by an Optical Fiber Technique", *Journal of Neuroscience Methods,* 2(1980)9–17, pp. 9–17.

Primary Examiner—David C. Nelms
Assistant Examiner—Michael Messinger
Attorney, Agent, or Firm—Birch, Stewart, Kolasch & Birch

[57] ABSTRACT

A fiberoptic probe for brain scanning formed on one end of a pair of incoming and outgoing optical conductors is disclosed. The probe comprises an armoring-pipe which covers the outside of the pair and is capable of retaining a cannula guide at least temporarily. This structure facilitates an accurate positioning of an infusion cannula for the subsequent experiments.

5 Claims, 8 Drawing Figures

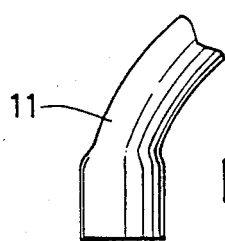
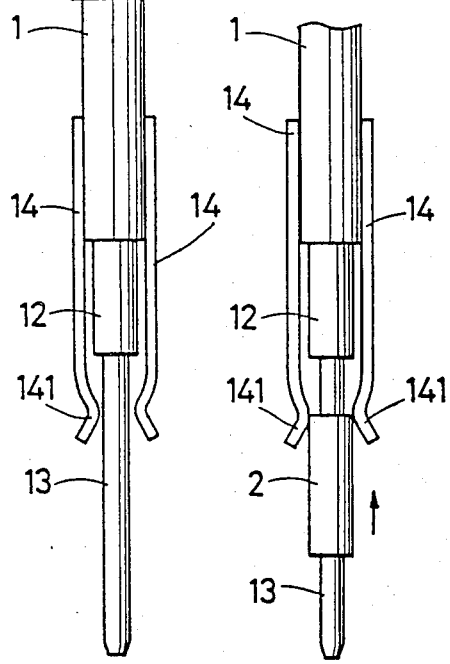
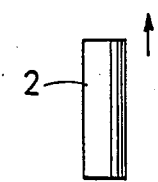
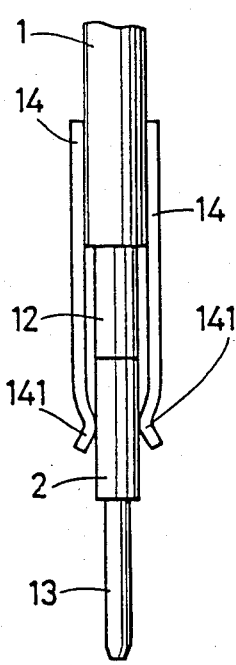
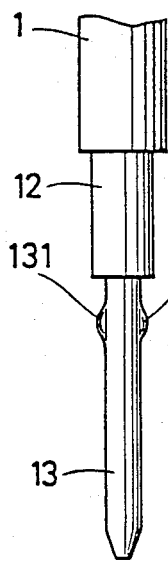
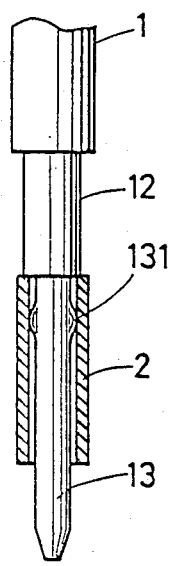

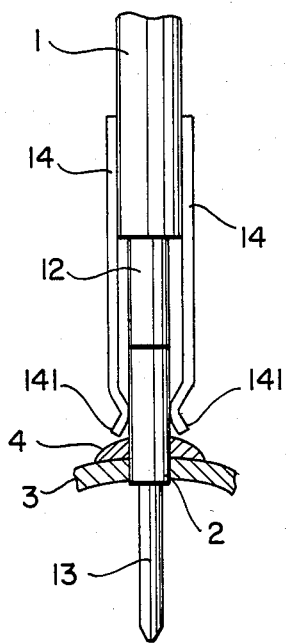
FIG. ID
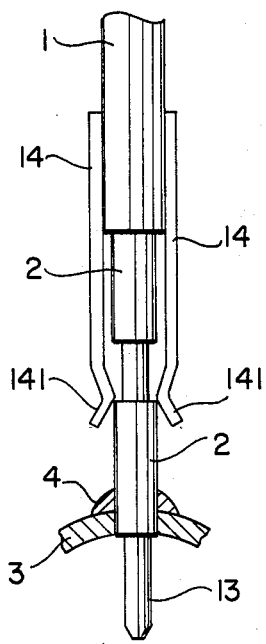
FIG. IE
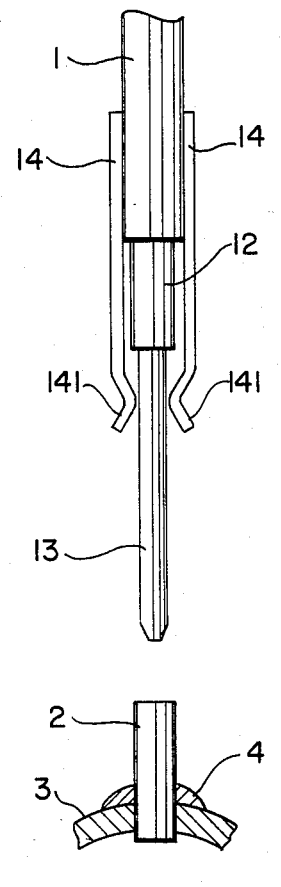
FIG. IF

FIBEROPTIC PROBE FOR BRAIN SCANNING WITH DETACHABLE CANNULA GUIDE

TECHNICAL FIELD

The present invention generally relates to the art of fiberoptic brain scanning of an experimental animal. Particularly, it is concerned with a fiberoptic probe equipped on one end of a flexible cord assembly for use in the art together with associated implements such as a photoelectric processor which provides light to be transmitted through an optical conductor into the brain tissues and processes the light signal returned from the tissues to present the scanning results as a chart and a probe driving means mounted on a conventional stereotaxic instrument. The fiberoptic probe retains, at least temporarily, a detachable cannula guide.

DESCRIPTION OF THE PRIOR ART

A method is known for scanning brain tissues of an experimental animal by detecting the differences in reflectance in a particular site of the brain tissue while a pair of glass optical fiber is advanced through the brain. Light is transmitted through one of the pair of the optical fibers to a spot of the tissue where the light is reflected or dispersed. Only the reflected light is picked up at the distal end of the pair and sent back through the other of the pair to be sensed and read. As the tip of the pair of fibers advance, the read-out signal varies accordingly, and the signal may be recorded by any means such as a pen-writing recorder.

Since the brain tissue usually has characteristically different conditions for light dispersion or reflection at its specific locality, the above-mentioned read-out value or recorded chart, i.e., brain map, supplies detailed information about the brain tissue. Thus, one can easily specify a spot and make it an indicator for conducting subsequent experiments. The spot is a limited brain region where (an) electrode(s) or (a) cannula(e) should be accurately placed or embedded.

Drugs which can participate in or induce a biochemical reaction therein may be infused into the spot through the cannula. In addition to the pick-up of spontaneous biological electric signal from the brain tissue, the embedded electrode may supply the brain with an electric energy which stimulates the nerve fiber or initiates an electrochemical reaction therein.

The fundamental concept of this valuable technique has already been disclosed by the present inventors (See, for instance, Journal of Neuroscience Method, 2 (1980), 9-17).

Incidentally, in order to continuously or intermittently inject a drug into a specific site of the brain searched out as a result of the above-mentioned scanning operation, an infusion cannula should accurately be guided when placed. If the infusion cannula is selected to have a constant length from its tip end to root stopper and a cannula guide which can sheath the infusion cannula is fixed to the cranial bones (with, for instance, dental cement), the infusion cannula can always be guided to an accurate position.

Normally, the rigid thin pipe, the constituent of the probe for penetrating into brain tissues, is structured to have a notched configuration, i.e., a stepwisely increasing of diameters from the smallest at its tip end to the largest at its root. Therefore, if a cannula guide or pipe with both ends open having an inside diameter suited for the outside diameter of the penetrating section of the probe is fitted to the penetrating section to be retained at a predetermined position thereof with an adhesive tape or agent of ralatively poor adhesive ability, the pipe with both ends open may be glued on the cranial bone during the scanning operation.

It can thereafter be retained there at the completion of the scanning by pulling the probe out. However, it is difficult for the operator to retain the cannula guide on the probe beforehand with an adhesive tape or the like. Therefore, it is convenient if the cannula guide is retained on the penetrating segment, at least temporarily, without any adhesive means.

The armoring-pipe of the probe covers a pair of optical conductors, one of which transmits light to the brain tissues and the other receives the reflected light, and is capable of collecting information within the brain in a manner as previously described.

SUMMARY OF THE INVENTION

As a result of continued investigation on the above-mentioned technique, the present inventors have now devised a practical and useful structure of the probe which facilitates the subsequent infusion operation.

According to the present invention, there is provided a fiberoptic probe for brain scanning formed on one end of a pair of incoming and outgoing optical conductors which comprises; an armoring-pipe which covers the outside of said pair and retains, at least temporarily, a detachable cannula guide thereon.

The armoring-pipe may comprise a plurality of rigid thin pipes whose diameters are varied to form a stepped configuration. The armoring-pipe may have at least a penetrating section diameter and a root section of larger to than the penetrating section form a step therebetween. Said larger diameter root section may comprise at least one clamp means made of a resilient material capable of retaining said cannula guide accomodated on said penetrating section, preferably at a position adjacent to the step.

DESCRIPTION OF THE INVENTION

The armoring-pipe may preferably have a notched configuration. The cannula guide may usually be held at a predetermined position, usually at one adjacent to the notch, preferably by a pair of clamps. The ends of the clamps are fixed to the pipe at the root section and the tips thereof extend to the penetrating section. Since the clamp is made of a resilient material so that it does not hinder the accomodating operation of the cannula guide but does retain the guide once it is accomodated by pressing inwards, the guide can rest at the predetermined position until it is forced to be pulled out.

Alternatively, the upper part of the penetrating section may be expanded to form a lobe or the like and said expanded part is made sufficiently large to retain the inserted guide by pressing outwards in order to fulfil the same object.

The cannula guide may also be a simple stainless steel thin pipe with both ends open which is similar to that used for structuring the armoring-pipe.

During the scanning operation, the detachable cannula guide accomodated on the penetrating section of the armoring-pipe is glued on the cranial bones around its periphery with dental cement or the like, and when the operation is completed by pulling the probe out from the brain, the stainless pipe is left in position on the cranial bones as the cannula guide, which may subsequently be used in accurately positioning a cannula for drug infusion.

In the following paragraphs, the present invention will be described in more detail by referring to the preferred embodiments shown in the attached drawings wherein the same components are designated by the same reference numerals throughout the several views.

DESCRIPTION OF THE DRAWINGS

FIGS. 1A, 1B and 1C are enlarged partial schematic views showing the probe encased in the armoring-pipe with clamp means built in accordance with the present invention and the cannula guide to be accomodated thereto, in varying degrees of the accomodating operation, FIG. 1D is an enlarged partial schematic view of the cannula guide cemented in place, FIGS. 1E and 1F are enlarged partial schematic views showing varying degrees of the detaching operation, and FIGS. 2A and 2B are enlarged partial schematic views representing a part of the probe encased in the armoring-pipe equipped with another means for retaining the guide which is shown in section in FIG. 2B.

DESCRIPTION OF THE PREFERRED EMBODIMENTS

In FIG. 1, an armoring-pipe of the probe is composed of thin stainless steel pipes 1, 12 and 13 invested one with the other to form the shown stepped configuration (about 1060 $\mu$m, 630 $\mu$m and 310 $\mu$m in the outside diameters). Inside the armoring-pipe, a pair of optical conductors (not shown) is glued together with the pipes. Numeral 11 is a flexible sheath for reinforcing the connection of the joint of the armoring-pipe with a flexible segment of the assembly.

The outside diameter of the penetrating section 13 is slightly smaller than the inside diameter of a cannula guide 2 of plain stainless steel pipe. A pair of clamp means 14 made of a resilient material is fixed to the largest diameter section 1 of the armoring-pipe.

In FIG. 1A, the cannula guide 2 is shown to be ready for accomodation around the periphery of the penetrating section 13 of the probe, wherein the direction of the guide's movement is indicated by an arrow.

In FIG. 1B, the guide 2 is already accomodated midway around the section but does not reach its rest position by being blocked slightly by the tips 141 of the clamps 14. In FIG. 1C, the guide 2 is placed at a position adjacent to the lower notch, i.e., the lower end of the pipe 12, where the guide 2 is pressed inwards by the tips 141 of the pair of the resilient clamps 14 attached to the root section of the pipe 1 by soldering or the like means.

At this rest position, the guide 2 is glued to the cranial bones 3 of the test animal with dental cement 4 or the like and when the searching operation is completed by pulling the probe 1 out from the brain, the guide 2 is left glued on the bones by movement of the probe in the in the manner illustrated in FIGS. 1E and 1F.

FIGS. 2A and 2B illustrate another embodiment of the guide retaining means, wherein at least one lobe 131 is provided on the penetrating section 13 of the probe armoring-pipe. FIG. 2B shows its state wherein the guide 2 is at rest at a position adjacent to the lower notch and retained there by being pressed outwards by the lobe 131. The same function as that of the lobe 131 may obviously be expected with any expanded part provided on the penetrating section 13.

What is claimed is:

1. A fiberoptic probe for brain scanning formed on one end of a pair of incoming and outgoing optical conductors which comprises; and armoring-pipe which covers the outside of said pair and includes means for retaining, at least temporarily, a detachable cannula guide thereon.

2. A probe as claimed in claim 1, wherein said armoring-pipe comprises a plurality of rigid sections whose diameters are varied to form a stepped configuration.

3. A probe as claimed in claim 2, wherein said armoring-pipe sections comprise a penetrating section and a root section of larger diameter than said penetrating section to form a step therebetween.

4. A probe as claimed in claim 3, wherein said retaining means comprises at least one clamp means made of resilient material capable of retaining said cannula guide accomodated on said penetrating section.

5. A probe as claimed in claim 3, wherein said retaining means comprises at least one enlarged portion of said penetrating section which fits within said cannula guide to retain the latter by friction.

* * * * *